(12) United States Patent
Bateson et al.

(10) Patent No.: US 6,211,212 B1
(45) Date of Patent: Apr. 3, 2001

(54) PYRROLIDINE AND THIAZOLE DERIVATIVES WITH METALLO-BETA-LACTAMASE INHIBITORY PROPERTIES

(75) Inventors: John Hargreaves Bateson, Sawbridgeworth; Desmond John Best, Ware, both of (GB)

(73) Assignee: SmithKline Beecham p.l.c., Brentford (GB)

( * ) Notice: Subject to any disclaimer, the term of this patent is extended or adjusted under 35 U.S.C. 154(b) by 0 days.

(21) Appl. No.: 09/367,610

(22) PCT Filed: Feb. 24, 1998

(86) PCT No.: PCT/EP98/01272

§ 371 Date: Aug. 17, 1999

§ 102(e) Date: Aug. 17, 1999

(87) PCT Pub. No.: WO98/40056

PCT Pub. Date: Sep. 17, 1998

(30) Foreign Application Priority Data

Mar. 13, 1997 (GB) .................................. 97051882
Mar. 13, 1997 (GB) .................................. 97051940

(51) Int. Cl.[7] ...................... A61K 31/425; A61K 31/195; A61K 31/24; C07D 277/04; C07D 321/00

(52) U.S. Cl. ........................ 514/365; 514/562; 514/541; 548/201; 562/426; 560/9

(58) Field of Search ............................ 548/201; 562/426; 560/9; 514/365, 562, 541

(56) References Cited

FOREIGN PATENT DOCUMENTS

| WO 95/09634 | 4/1995 | (WO) . |
| WO 96/04242 | 2/1996 | (WO) . |
| WO 97/10225 | 3/1997 | (WO) . |

OTHER PUBLICATIONS

Chemical Abstract, vol. 108, No. 25, 1988, Columbus, Ohio, US; abstract No. 222071M, Chen et al.: "Synthesis of N–(2–mercaptobenzoy)–N–(alkynl/ary)–glycines and the corresponding disulfides" p. 612.

Primary Examiner—Deborah C. Lambkin
(74) Attorney, Agent, or Firm—James M. Kanagy; Charles M. Kinzig

(57) ABSTRACT

A method of treatment of bacterial infections in humans or animals which comprises administering, in combination with a β-lactam antibiotic, a therapeutically effective amount of an amino acid derivative or a pharmaceutically acceptable salt, solvate or in vivo hydrolysable ester thereof.

15 Claims, No Drawings

PYRROLIDINE AND THIAZOLE DERIVATIVES WITH METALLO-BETA-LACTAMASE INHIBITORY PROPERTIES

This application is a 371 of PCT/EP98/01272 Feb. 24, 1998.

This invention relates to chemical compounds having metallo-β-lactamase inhibitory and antibacterial properties. The invention also relates to methods for the preparation of such compounds, to pharmaceutical compositions containing them, and to uses thereof.

Metallo-β-lactamases confer resistance to the vast majority of β-lactam based therapies, including carbapenems and jeopardise the future use of all such agents. As a result of the increased use of carbapenems and other β-lactam antibiotics the clinical climate is becoming more favourable for the survival of clinical strains which produce metallo-β-lactamases, and metallo-β-lactamases have now been identified in common pathogens such as *Bacillus fragilis*, *Klebsiella*, *Pseudomonas aeruginosa* and *Serratia marcescens*. Emerging knowledge emphasises that metallo-β-lactamases have the potential to present a crisis situation for antimicrobial chemotherapy.

U.S. Pat. No. 4,513,009 discloses amino acid derivatives including thiorphan having enkephalinase-inhibiting, antalgic, antidiarrhea and hypotensive. Analgesic effects are disclosed for thiorphan (B. P. Roques et al, *Nature*, 1980, 288, 286) and for other mercapto amino acid derivatives (JO 3002-117-A). Mercapto amino acid derivatives are disclosed as inhibitors of angiotensin-converting enzyme (ACE) (J. L. Stanton, et al, *J. Med Chem.*, 1983, 26, 1257, U.S. Pat. No. 4,053,651 and GB 2090-591); as conferring antihypotensive effects (WO 9308162); as enkephalinase (neutral endopeptidase (NEP)) inhibitors (U.S. Pat. No. 4,474,799 and Mimura et al, *J. Med. Chem.*, 1992, 35, 602 and references cited therein); as dual inhibitors of ACE and NEP (Fournie-Zaluski et al., *J. Med. Chem.*, 1994, 37(8), 1070, WO 9417036 and *Bioorg. Med. Chem. Lett.*, 1996, 6(17), 2097); as inhibitors of endothelin-converting enzyme (ECE) (WO 9311154, Burtenshaw, et al, *Bioorg. Med. Chem. Lett.*, 1993, 3(10), 1953 and Deprez et al., *Bioorg. Med. Chem. Lett.*, 1996, 6(19)); as metalloproteinase inhibitors (WO 9425435); and having radioprotective action and cytotoxicity (M. Hikita et al, *J. Radiat. Res.*, 1975, 16(3), 162 and DE2,349, 707). DE3819539 (Squibb) discloses amino acids and peptide derivatives as inhibitors of neutral endopeptidase and their use as antihypertensives and diuretics. U.S. Pat. No. 4,046,889, U.S. Pat. No. 4,105,776, U.S. Pat. No. 4,307,110, U.S. Pat. No. 4,316,906, BE868532, CH635087, J55057561, J55009060, U.S. Pat. No. 428,340 and EP0001978 disclose various substituted proline and thiazolidine compounds having anti-hypertensive activity.

Other references to amino acid derivatives having the abovementioned activities include: Gordon et al., Life Sciences 1983, 33 (Supp. I), 113–6; Waller et al., J, Med. Chem. 1993, 36, 2390–2403; Saunders et al., J. Comp. Aided Mole. Des. 1987, 1, 133–42; Gomez-Monterrey et al., J. Med. Chem. 1993, 36, 87–94; Oya et al., Chem. Pharm. Bull. 1981, 29(4), 940–7; Trapani et al., Biochem. Mol. Biol. Int 1993, 31(5), 861–7; Baxter et al., J. Med. Chem. 1992, 35(20), 3718–20; Condon et al., J. Med. Chem. 1982, 25(3), 250–8; Cheung et al., J. Biol. Chem. 1980, 255(2), 401–7; Cushman et al., Biochemistry 1977, 16(25), 5484–91; EP0539848, EP0419327, EP0254032, EP0355784, EP0449523, EP0153755, U.S. Pat. No. 5,061,710, U.S. Pat. No. 4,339,600, U.S. Pat. No. 4,401,677, U.S. Pat. No. 4,199,512, DE2717548, DE2711225, JP54052073, JP54063017, JP54092937, JP55055165, JP54063017, WO940748 1, WO8202890 and BE890398.

Other amino acid derivatives are described by: Fuchs et al., Arzneim.-Forsch 1985, 35(9)1394–402, having mitochondrial dysfunction and postischemic myocardial damage activity; Rajkovic et al., Biochem. Pharmacol. 1984, 33(8), 1249–50, having enhancement of neutrophil response and modulation of superoxide and hydrogen peroxide production; Sakurai et al., Chem. Pharam. Bull. 1979, 27(12), 3022–8 forming a peptide/cytochrome P450 heme system; and Sugiura et al., J. Am. Chem. Soc. 1977, 99(5), 1581–5, forming copper(II) and nickel(II) complexes.

(1S, 2R, 5S)— and (1R, 2S, 5R)—isomers of [(2-mercapto-5-phenyl cyclopentanecarbonyl)-amino]-acetic acid are reported as inhibitors both of thermolysin and of neutral endopeptidase (Fillion et al, Biorg. Med. Chem. Lett, 1996, 6 (17), 2097–2102). N-(2-mercaptobenzoyl) derivatives of glycine and the L-amino acids are disclosed as possessing thymulin-like activity (Morita, et al, JP03176465 A2, 1991), as ACE inhibitors (Yun-Choi, et al, Yakhak Hoechi, 1988, 31 (1), 1–9) and as synthetic intermediates for the prepraration of disulphides (Lu. et al, Zhongguo Yaoke Daxue Xuebao, 1990, 21 (1), 1–5).

WO97/10225 (published 20.03.97) and WO97130027 (published 21.08.97) disclose certain amino acid derivatives which have metallo-β-lactamase inhibitory properties, and are useful for the treatment of infections in animals.

A further series of amino acid derivatives have now been discovered, which compounds have metallo-β-lactamase inhibitory properties, and are useful for the treatment of infections in animals.

According to the present invention there is provided a method of treatment of bacterial infections in humans or animals which comprises administering, in combination with a β-lactam antibiotic, a therapeutically effective amount of a compound of formula (IA), (IB) or (IC) or a pharmaceutically acceptable salt, solvate or in vivo hydrolysable ester thereof:

(IA)

$$R_4S\text{---}CH(R_5)\text{---}CH(R_3)\text{---}CON(R_2^A)\text{---}\overset{*}{C}H(R_1^A)\text{---}CO_2R$$

(IB)

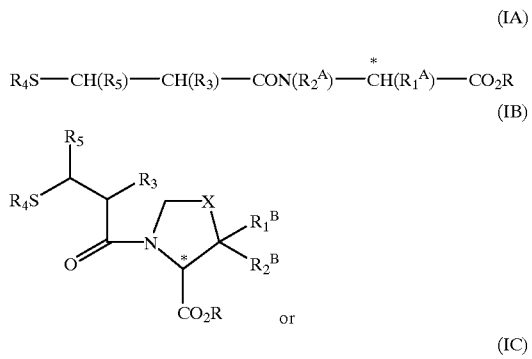

or (IC)

$$R_4S\text{---}CH(R_5)\text{---}CH(R_3)\text{---}CON(R_2^C)\text{---}\overset{*}{C}H(R_1^C)\text{---}CO_2R$$

wherein:

R is hydrogen, a salt forming cation or an in vivo hydrolysable ester-forming group;

$R_1^A$ is hydrogen, $(C_{1-6})$alkyl optionally substituted by up to three halogen atoms or by a mercapto, $(C_{1-6})$alkoxy, hydroxy, amino, nitro, carboxy, $(C_{1-6})$ alkylcarbonyloxy, $(C_{1-6})$alkoxycarbonyl, formyl or $(C_{1-6})$alkylcarbonyl group, $(C_{3-7})$cycloalkyl, $(C_{3-7})$cycloalkyl$(C_{2-6})$alkyl, $(C_{2-6})$alkenyl, $(C_{2-6})$alkynyl, aryl arly$(C_{1-6})$alkyl, heterocyclyl or heterocyclyl$(C_{1-6})$alkyl;

$R_2^A$ is hydrogen, $(C_{1-6})$alkyl or aryl$(C_{1-6})$alkyl;

$R_1^B$ and $R_2^B$ are each hydrogen or an organic substituent group;

$R_1^C$ is selected from

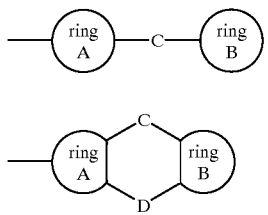

(a)

(b)

in which A is a monocyclic aryl or heteroaryl ring and B is a monocyclic aryl, alicyclic or heterocyclic ring, C and D are independently $-Z_p\text{-}(CR_8R_9)_q-$ or $-(CR_8R_9)_q-Z_p$ where p is 0 or 1, q is 0 to 3 provided that p+q in C is not 0, $R_8$ and $R_9$ are independently hydrogen or $(C_{1-6})$alkyl or together represent oxo and Z is O, $NR_{10}$ or S(O)x where $R_{10}$ is hydrogen, $(C_{1-6})$ alkyl or aryl$(C_{1-6})$alkyl and x is 0–2, and wherein C and D are linked ortho to one another on each of rings A and B in formula (b);

$R_2^C$ is hydrogen, $(C_{1-6})$alkyl or aryl$(C_{1-6})$alkyl;

$R_3$ and $R_5$ together complete a carbocyclic ring having 4 to 8 ring atoms, which may be saturated, unsaturated or aromatic, optionally fused to a phenyl ring, and optionally substituted by 1–3 halo, phenyl, $(C_{1-6})$alkoxy optionally substituted by 1–3 halo, hydroxy$(C_{1-6})$alkyl, mercapto$(C_{1-6})$alkyl, hydroxy, $CO_2R_7$, $N(R_7)_2$ or $CON(R_7)_2$ where each $R_7$ is independently hydrogen or $(C_{1-6})$ alkyl, $OCONH_2$, nitro, $(C_{1-6})$ alkylcarbonyloxy, $(C_{1-6})$alkoxycarbonyl$(C_{1-6})$alkyl, formyl, or $(C_{1-6})$ alkylcarbonyl groups; and $R_4$ is hydrogen, or an in vivo hydrolysable acyl group.

The compounds of formulae (IA), (IB) and (IC), hereinafter 'formula (I)' may exist in a number of isomeric forms, all of which, including racemic and diastereoisomeric forms, are encompassed within the scope of the present invention.

It is preferred that the stereochemistry at the carbon atom marked * is D-.

The term 'aryl' includes phenyl and naphthyl, each optionally substituted with up to five, preferably up to three, groups selected from halogen, mercapto, $(C_{1-6})$alkyl optionally substituted by 1–3 halo, phenyl, $(C_{1-6})$alkoxy optionally substituted by 1–3 halo, hydroxy$(C_{1-6})$alkyl, mercapto$(C_{1-6})$ alkyl, hydroxy, $CO_2R_7$, $N(R_7)_2$ or $CON(R_7)_2$ where each $R_7$ is independently hydrogen or $(C_{1-6})$alkyl, $OCONH_2$, nitro, $(C_{1-6})$alkylcarbonyloxy, $(C_{1-6})$alkoxycarbonyl$(C_{1-6})$alkyl, formyl, or $(C_{1-6})$ alkylcarbonyl groups.

Each alicyclic ring suitably has from 4 to 7, preferably 5 or 6, ring carbon atoms.

Alicyclic rings may be unsubstituted or substituted by, for example, up to five, preferably up to three, groups selected from those mentioned above for substitution on aryl.

The terms 'heterocyclyl' and 'heterocyclic' as used herein include aromatic and non-aromatic, single and fused, rings suitably containing up to four hetero-atoms in each ring selected from oxygen, nitrogen and sulphur, which rings may be unsubstituted or substituted by, for example, up to three groups selected from those mentioned above for substitution on aryl and, for non-aromatic heterocyclic rings, oxo groups. Each heterocyclic ring suitably has from 4 to 7, preferably 5 or 6, ring atoms. The term 'heteroaryl' refers to heteroaromatic heterocyclic ring or ring system, suitably having 5 or 6 ring atoms in each ring. A fused heterocyclic ring system may include alicyclic rings and need include only one heterocyclic ring. Examples of heterocyclyl groups include indolyl, thienyl, isoimidazolyl, thiazolyl, furyl, quinolinyl, imidazolidinyl and benzothienyl. Compounds within the invention containing a heterocyclyl group may occur in two or more tautomeric forms depending on the nature of the heterocyclyl group; all such tautomeric forms are included within the scope of the invention.

When used herein the terms 'lower alkyl', 'lower alkenyl', 'lower alkynyl' and 'alkoxy' include straight and branched chain groups containing from 1 to 6 carbon atoms, such as methyl, ethyl, propyl and butyl. A particular alkyl group is methyl.

When used herein the term 'halogen' refers to fluorine, chlorine, bromine and iodine.

Although racemic and other mixtures of (*) D- and L-diastereomers of known compounds of formula (I) have been described, there has been little or no attempt to isolate pure D-isomers as herein defined because the antihypertensive activity of the compounds has been found to reside predominantly in the L-isomer.

Certain compounds of formula (I) including compounds of formula (IB) and (IC), and compounds of formula (IA) where $R_1^A$ is aryl or heterocyclyl are novel and as such form part of the invention. Compounds of formula (IA) in which $R_1^A$ is aryl or heteroaryl are hereafter referred to as compounds of formula (ID).

Examples of $R_1^A$ optionally substituted alkyl include methyl, isobutyl, carboxymethyl, mercaptomethyl and 1-hydroxyethyl. Examples of $R_1$ arylalkyl include optionally substituted benzyl. Examples of $R_1$ aryl include phenyl optionally substituted with up to five, preferably up to three, groups selected from halogen, mercapto, $(C_{1-6})$ alkyl, phenyl, $(C_{1-6})$alkoxy, hydroxy$(C_{1-6})$alkyl, mercapto$(C_{1-6})$ alkyl, halo$(C_{1-6})$ alkyl, hydroxy, amino, nitro, carboxy, $(C_{1-6})$alkylcarbonyloxy, $(C_{1-6})$alkoxycarbonyl, formyl or $(C_{1-6})$ alkylcarbonyl groups, preferably unsubstituted phenyl. Examples of $R_1^A$ heteroaryl include indolyl, thienyl, isoimidazolyl, thiazolyl, furyl and benzothienyl, preferably 2-thienyl, 2-furyl or 2-benzothienyl. $R_1^A$ is most preferably unsubstituted phenyl.

Suitable examples of $R_2^A$ include hydrogen, methyl and benzyl.

$R_2^A$ is preferably hydrogen.

In general formula (I), $R_1^B$ and $R_2^B$ denotes hydrogen or an organic group. This may suitably be linked through a carbon atom. For example, $R_1^B$ or $R_1^B$ may represent hydrogen or a group of formula $-R^{10}$, where $R^{10}$ denotes an unsubstituted or substituted $(C_{1-10})$hydrocarbon group.

Preferably, $R_1^B$ or $R_2^B$ represents hydrogen, $(C_{1-10})$alkyl, aryl, heterocyclyl or substituted $(C_{1-10})$alkyl, wherein the substituent may be aryl, heterocyclyl, hydroxy, $(C_{1-6})$alkoxy, $(C_{1-6})$alkanoyloxy, halogen, mercapto, $(C_{1-6})$alkylthio, heterocyclylthio, amino, (mono or di)-$(C_{1-6})$alkylamino, $(C_{1-6})$alkanoylamino, carboxy, or $(C_{1-6})$alkoxycarbonyl.

Examples of suitable organic groups $R_1^B$ and $R_2^B$ include methyl, ethyl, propyl, hydroxymethyl, methoxymethyl, ethoxymethyl, acetoxymethyl, (1 or 2)-acetoxyethyl, aminomethyl, 2-aminoethyl, acetamidomethyl, 2-acetamidoethyl, carboxymethyl, phenyl, pyridyl, pyrimidyl and isoxazolyl.

In particular, $R_1^B$ and $R_2^B$ may be hydrogen or methyl.

X is preferably S.

In a preferred aspect, when $R_1^C$ is formula (a), ring A is selected from 2,5-thienyl, 2,5-furyl, 1,2-phenyl, 1,3-phenyl and 1,4-phenyl, ring B is selected from phenyl optionally substituted by one or two hydroxy or by methoxy, dimethylamino, carboxy or nitro, 2-furyl, 2-, 3- or 4-pyridyl, 1-tetrazolyl, 2-tetrazolyl, 1-triazolyl, 2-triazolyl, 2 thienyl and imidazolin-2,5-dione-1-yl and C is selected from $CH_2$, O or $OCH_2$. In a more preferred aspect $R_1^C$ is 4-benzyloxyphenyl 3- or 4-substituted in the benzyl group by an aryl substituent.

In another preferred aspect, when $R_1^C$ is formula (b), rings A and B are both phenyl, C is O, $CH_2$ or $NR_{10}$ and D is a bond (p+q=0).

Preferred examples of $R_1^C$ include (5-benzyl)thien-2-yl, (5-benzyl)furan-2-yl, 5-(1-tetrazolylmethyl)thien-2-yl, 5-(2-tetrazolylmethyl)thien-2-yl, 5-(imidazolin-2,5-dione-1-ylmethyl)thien-2-yl, 5-(2-triazolylmethyl)thien-2-yl, 5-(2-triazolylmethyl)thien-2-yl, 3-phenoxyphenyl, 2-phenoxyphenyl, 4-phenoxyphenyl, 3-(4-hydroxybenzyl) phenyl, 3-(4-methoxybenzyl)phenyl, 4-benzyloxyphenyl, 4-(2-thienylmethyloxy)phenyl, 1-fluorenyl, 3-(N-ethylcarbazolyl), 4-hydroxybenzyloxy-4-phenyl, 4-methoxybenzyloxy-4-phenyl, 4-dimethylaminobenzyloxy-4-phenyl, 4-carboxybenzyloxy-4-phenyl, 3-carboxybenzyloxy-4-phenyl, (2-pyridyl)-methoxy-4-phenyl, (4-pyridyl)-methoxy-4-phenyl, 5-[1-(4-carbamoyltriazolyl)-methyl]-thien-2-yl, 5-[1-(4-carboxytriazolyl)-methyl]-thien-2-yl, (2-furyl)-methoxy-4-phenyl and dibenzothieoyl.

Suitable examples of $R_2^C$ include hydrogen, methyl and benzyl.

$R_2^C$ is preferably hydrogen.

$R_3$ and $R_5$ preferably together represent $(CH_2)_3$ or $(CH_2)_4$ optionally fused to phenyl, or together complete a phenyl ring.

Examples of $R_4$ include hydrogen, lower alkylcarbonyl, optionally substituted benzoyl or optionally substituted phenyl lower alkyl carbonyl, more preferably hydrogen and acetyl.

$R_4$ is preferably hydrogen.

Suitable pharmaceutically acceptable salts of the carboxylic acid group of the compound of formula (I) (or of other carboxylic acid groups which may be present as optional substituents) include those in which R is a metal ion e.g. aluminium salts, alkali metal salts (e.g. sodium, lithium or potassium salts), alkaline earth metal salts (e.g. calcium or magnesium salts), ammonium salts, and substituted ammonium salts, for example those with lower alkylamines (e.g.triethylamine), hydroxy-lower alkylamines (e.g. 2-hydroxyethylamine), bis-(2-hydroxyethyl)amine, tris-(2-hydroxyethyl)amine, lower-cycloalkylamines (e.g. dicyclohexyl-amine), or with procaine, dibenzylamine, N,N-dibenzyl-ethylenediamine, 1-ephenamine, N-methylmorpholine, N-ethylpiperidine, N-benzyl-β-phenethylamine, dehydroabietylamine, ethylenediamine, N,N'-bishydroabietylethylenediamine, bases of the pyridine type (e.g. pyridine, collidine and quinoline), and other amines which have been or can be used to form quaternary ammonium salts.

Pharmaceutically acceptable salts may also be acid addition salts of any amino or substituted amino group(s) that may be present as optional substituents on the compound of formula (I), or of a heterocyclic group ring nitrogen atom. Suitable salts include for example hydrochlorides, sulphates, hydrogen sulphates, acetates, phosphates etc. and other pharmaceutically acceptable salts will be apparent to those skilled in the art. Suitable addition salts are the hydrochlorides and hydrogen sulphates.

Preferred salts are sodium salts.

Examples of suitable pharmaceutically acceptable in vivo hydrolysable ester-forming groups R include those forming esters which break down readily in the human body to leave the parent acid or its salt. Suitable groups of this type include those of part formulae (i), (ii), (iii), (iv) and (v):

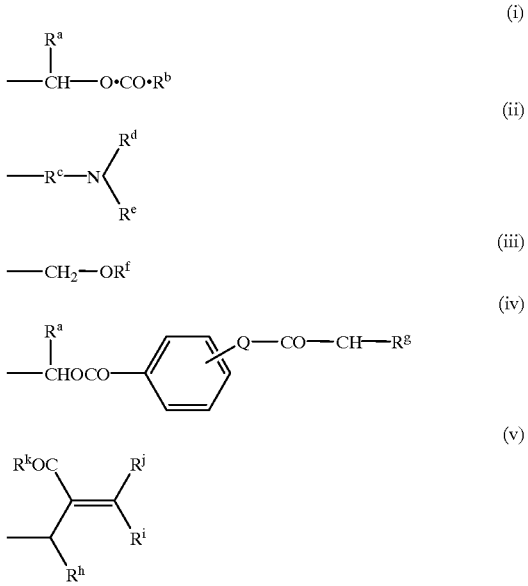

wherein $R^a$ is hydrogen, $(C_{1-6})$ alkyl, $(C_{3-7})$ cycloalkyl, methyl, or phenyl, $R^b$ is $(C_{1-6})$alkyl, $(C_{1-6})$alkoxy, phenyl, benzyl, $(C_{3-7})$cycloalkyl, $(C_{3-7})$cycloalkyloxy, $(C_{1-6})$alkyl $(C_{3-7})$cycloalkyl, 1-amino $(C_{1-6})$alkyl, or 1-$(C_{1-6}$alkyl)amino $(C_{1-6})$ alkyl; or $R^a$ and $R^b$ together form a 1,2-phenylene group optionally substituted by one or two methoxy groups; $R^c$ represents $(C_{1-6})$ alkylene optionally substituted with a methyl or ethyl group and $R^d$ and $R^e$ independently represent $(C_{1-6})$ alkyl; $R^f$ represents $(C_{1-6})$ alkyl; $R^g$ represents hydrogen or phenyl optionally substituted by up to three groups selected from halogen, $(C_{1-6})$alkyl, or $(C_{1-6})$ alkoxy; Q is oxygen or NH; $R^h$ is hydrogen or $(C_{1-6})$ alkyl; $R^i$ is hydrogen, $(C_{1-6})$ alkyl optionally substituted by halogen, $(C_{2-6})$ alkenyl, $(C_{1-6})$ alkoxycarbonyl, aryl or heteroaryl; or $R^h$ and $R^i$ together form $(C_{1-6})$ alkylene; $R^j$ represents hydrogen, $(C_{1-6})$ alkyl or $(C_{1-6})$ alkoxycarbonyl; and $R^k$ represents $(C_{1-8})$ alkyl, $(C_{1-8})$ alkoxy, $(C_{1-6})$ alkoxy$(C_{1-6})$alkoxy or aryl.

Examples of suitable in vivo hydrolysable ester-forming groups include, for example, acyloxyalkyl groups such as acetoxymethyl, pivaloyloxymethyl, α-acetoxyethyl, α-pivaloyloxyethyl, 1-(cyclohexylcarbonyloxy)prop-1-yl, and (1-aminoethyl)carbonyloxymethyl; alkoxycarbonyloxyalkyl groups, such as ethoxycarbonyloxymethyl, α-ethoxycarbonyloxyethyl and propoxycarbonyloxyethyl; dialkylaminoalkyl especially di-loweralkylamino alkyl groups such as dimethylaminomethyl, dimethylaminoethyl, diethylaminomethyl or diethylaminoethyl; 2-(alkoxycarbonyl)-2-alkenyl groups such as 2-(isobutoxycarbonyl)pent-2-enyl and 2-(ethoxycarbonyl) but-2-enyl; and lactone groups such as phthalidyl and dimethoxyphthalidyl.

A further suitable pharmaceutically acceptable in vivo hydrolysable ester-forming group is that of the formula:

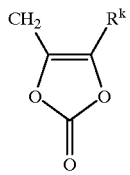

wherein $R^k$ is hydrogen, $C_{1-6}$ alkyl or phenyl.

R is preferably hydrogen.

It will be appreciated that also included within the scope of the invention are pharmaceutically acceptable salts and pharmaceutically acceptable esters, including in vivo hydrolysable esters, of any carboxy groups that may be present as optional substituents in compounds of formula (I).

Some compounds of formula (I) may be crystallised or recrystallised from solvents such as organic solvents. In such cases solvates may be formed. This invention includes within its scope stoichiometric solvates including hydrates as well as compounds containing variable amounts of solvents such as water that may be produced by processes such as lyophilisation. Compounds of formula (I) may be prepared in crystalline form by for example dissolution of the compound in water, preferably in the minimum quantity thereof, followed by admixing of this aqueous solution with a water miscible organic solvent such as a lower aliphatic ketone such as a di-($C_{1-6}$) alkyl ketone, or a ($C_{1-6}$) alcohol, such as acetone or ethanol.

The compounds of formula (I) are metallo-β-lactamase inhibitors and are intended for use in pharmaceutical compositions. Therefore it will readily be understood that they are preferably each provided in substantially pure form, for example at least 60% pure, more suitably at least 75% pure and preferably at least 85% pure, especially at least 95% pure particularly at least 98% pure (% are on a weight for weight basis). Impure preparations of the compounds may be used for preparing the more pure forms used in the pharmaceutical compositions; these less pure preparations of the compounds should contain at least 1%, more suitably at least 5% and preferably from 10 to 59% of a compound of the formula (I) or salt, solvate or in vivo hydrolysable ester thereof.

The present invention also provides a process for the preparation of a compound of formula (IB), (IC) or (ID) as defined above, which comprises reacting a compound of formula (II)

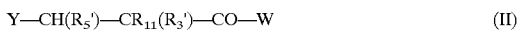
Y—CH($R_5$')—C$R_{11}$($R_3$')—CO—W    (II)

with a compound of formula (IIIA), (IIIB) or (IIIC)

$X^1$—CH($R_1^{A'}$)—$CO_2R^x$    (IIIA)

(IIIB)

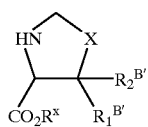

or

$X^1$—CH($R_1^{C'}$)—$CO_2R^x$    (IIIC)

wherein W is a leaving group, Y is Y' where Y' is $R_4$'S or a group convertible thereto and $R_{11}$ is H, or Y and $R_{11}$ together form a bond, $R^x$ is R or a carboxylate protecting group, $X^1$ is $N_3$, $NHR_2^{A'}$ or $NHR_2^{C'}$ and $R_1^{A'}$, $R_2^{A'}$, $R_1^{B'}$, $R_2^{B'}$, $R_1^{C'}$, $R_2^{C'}$, $R_3'$, $R_4'$ and $R_5'$ are $R_1^A$, $R_2^A$, $R_1^B$, $R_2^B$, $R_1^C$, $R_2^C$, $R_3$, $R_4$ and $R_5$ or groups convertible thereto, wherein R, $R_1^A$, $R_2^A$, $R_1^B$, $R_2^B$, $R_1^C$, $R_2^C$, $R_3$, $R_4$ and $R_5$ are as defined in formula (I), and thereafter, where Y and $R_{11}$ form a bond, reacting the product with a nucleophilic sulphur reagent Y'H, where necessary, converting Y' into $R_4$'S, converting $R^X$, $R_1^{A'}$, $R_2^{A'}$, $R_1^{B'}$, $R_2^{B'}$, $R_1^{C'}$, $R_2^{C'}$, $R_3'$0 $R_4'$ and/or $R_5'$ into R, $R_1^A$, $R_2^A$, $R_1^B$, $R_2^B$, $R_1^C$, $R_2^C$, $R_3$, $R_4$ and/or $R_5$ and optionally inter-converting R, $R_1^A$, $R_2^A$, $R_1^B$, $R_2^B$, $R_1^C$, $R_2^C$, $R_3$, $R_4$ and/or $R_5$.

Suitable ester-forming carboxyl-protecting groups $R^X$ other than in vivo hydrolysable ester forming groups are those which may be removed under conventional conditions. Such groups for $R^X$ include methyl, ethyl, benzyl, p-methoxybenzyl, benzoylmethyl, p-nitrobenzyl, 4-pyridylmethyl, 2,2,2-trichloroethyl, 2,2,2-tribromoethyl, t-butyl, t-amyl, allyl, diphenylmethyl, triphenylmethyl, adamantyl, 2-benzyloxyphenyl, 4-methylthiophenyl, tetrahydrofur-2-yl, tetrahydropyran-2-yl, pentachlorophenyl, acetonyl, p-toluenesulphonylethyl, methoxymethyl, a silyl (such as trimethylsilyl), stannyl or phosphorus- containing group or an oxime radical of formula —N=CH$R_{12}$ where $R_{12}$ is aryl or heterocyclyl, or an in vivo hydrolysable ester radical such as defined above.

Certain compounds of formulae (II), (IIIA), (IIIB) and (IIIC) may include an amino group which may be protected. Suitable amino protecting groups are those well known in the art which may be removed under conventional conditions if required without disruption of the remainder of the molecule.

Examples of amino protecting groups include ($C_{1-6}$) alkanoyl; benzoyl; benzyl optionally substituted in the phenyl ring by one or two substituents selected from ($C_{1-4}$) alkyl, ($C_{1-4}$) alkoxy, trifluoromethyl, halogen, or nitro; ($C_{1-4}$) alkoxycarbonyl; benzyloxycarbonyl or trityl substituted as for benzyl above; allyloxycarbonyl, trichloroethoxycarbonyl or chloroacetyl.

When $X^1$ in the compound of formula (IIIA) or (IIIC) is $NHR_2'$, the compound is preferably presented as the anion prepared by treatment of the amine with an organic base such as triethylamine, pyridine or morpholine, and suitable examples of the leaving W group in the compound of formula (II) include halo such as chloro and mixed sulphonic anhydrides such as those where W is methanesulphonyloxy, toluene-p-sulphonyloxy or trifluoromethanesulphonyloxy in mixed sulphonic anhydrides. The compound of formula (IIIA) or (IIIC) may be presented as the trimethylsilyl ester hydrochloride.

The reaction of the compounds of formula (II), (IIIA), (IIIB) and (IIIC) is preferably carried out at ambient temperature, for example 15–25° C., in an inert solvent such as chloroform tetrahydrothieo, dichloromethane, dioxan or dimethylformamide.

When $X^1$ in the compound of formula (IIIA) or (IIIC) is $N_3$, the leaving group W in the compound of formula (II) is preferably SH and the reaction is carried out at elevated temperature, such as at reflux, in an inert solvent such as toluene.

Examples of Y' convertible into $R_4$'S include halo such as bromo which may be displaced by thiobenzoic acid or thioacetic acid.

Where $R_{11}$ and Y together represent a bond, the group $R_4$'S may be introduced by addition of a nucleophilic sulphur reagent Y'H. Y' is $R_4$'S or a group convertible thereto. Thiolacetic acid is a suitable sulphur reagent.

Examples of groups $R_1^{A'}$, $R_2^{A'}$, $R_1^{B'}$, $R_2^{B'}$, $R_1^{C'}$, $R_2^{C'}$, $R_3'$, $R_4'$ and $R_5'$ convertible to $R_1^A$, $R_2^A$, $R_1^B$, $R_2^B$, $R_1^C$, $R_2^C$, $R_3$, $R_4$ and $R_5$ include those where any carboxy or amino group is protected by carboxy or amino protecting groups. Additionally, examples of $R_1^{C'}$ convertible to $R_1^C$ include those containing ring A substituted by hydroxy which can generate $R_1^C$ groups of formula (a) where linker C is of the form —O—$(CR_8R_9)_q$— and where ring B is an aromatic ring or heterocycle, optionally substituted. This may be effected, for example, by alkylation of the hydroxy substituent with a benzyl bromide derivative or with a heterocyclylalkyl bromide derivative. Alternatively, the hydroxy group may be coupled with a benzyl alcohol derivative or with a heterocyclylalkyl alcohol derivative in established ways, for example in the presence of diethyl azodicarboxylate and triphenylphosphine (Mitsunobo et al, *Bull. Chem. Soc. Jpn.*, 1967, 40, 2380).

$R_4'$ in the compound of formula (II) is preferably other than hydrogen, such as an acyl protecting group as described above for carboxy protecting groups, for example acetyl.

The acid derivative of formula (II) is preferably prepared from the corresponding free acid by treatment with strong base such as sodium hydride followed by a source of the anion leaving group W, such as oxalyl chloride where W is Cl, or hydrogen sulphide where W is SH.

The initial product of the reaction of compounds of formulae (II) and (IIIA), (IIIB) or (IIIC) is a compound of formula (IVA), (IVB or(IVC):

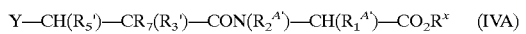
$$Y—CH(R_5')—CR_7(R_3')—CON(R_2^{A'})—CH(R_1^{A'})—CO_2R^x \quad (IVA)$$

(IVB)

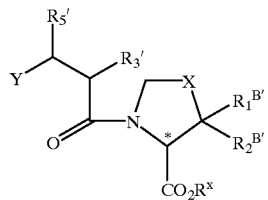

or

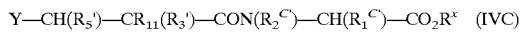
$$Y—CH(R_5')—CR_{11}(R_3')—CON(R_2^{C'})—CH(R_1^{C'})—CO_2R^x \quad (IVC)$$

wherein the variables are as defined in formulae (II), (IIIA), (IIIB and (IIIC). Novel intermediates of formula (IVA), (IVB) and (IVC) wherein $R^X$ is other than R when $R_1^{A'}$, $R_2^{A'}$, $R_1^{B'}$, $R_2^{B'}$, $R_1^{C'}$, $R_2^{C'}$, $R_3'$, $R_4'$ and $R_5'$ are $R_1^A$, $R_2^A$, $R_1^B$, $R_2^B$, $R_2^C$, $R_3$, $R_4$ and $R_5$ also form part of the invention.

Compounds of formula (IV) where $R_1^{C'}$ is —(A)—OH or —(A)—$CH_2OH$ may be converted to compounds with $R_1^C$ as defined in (a) where C is —$OCH_2$— or —$CH_2O$— using alcohols of formula (B')—$CH_2OH$ or (B')—OH, respectively under Mitsunobu conditions (Synthesis 1981, 1), using a coupling reagent such as triphenyl phosphine and diethyl azodicarboxylate. B' is B or a group convertible thereto, for example where a carboxy or amino substituent on B is protected.

When $R^X$ is other than hydrogen, the carboxy group —$COOR^X$ may be deprotected, that is to say, converted to a free carboxy, carboxy salt or carboxy ester group —COOR in a conventional manner, for example as described in EP0232966A.

Simultaneous deprotection of —$COOR_X$ and $R_4$,S and any protecting group in $R_1^{C'}$ may be achieved by treatment with sodium sulphide nonahydrate in water/methanol.

When it is desired to obtain a free acid or salt of the preferred isomer of the formula (I) from an isomeric mixture, this may be effected by chromatographic separation of the diastereomers of the product. Where this is an ester and/or where $R_4'$ is other than hydrogen, the desired isomer may then be deprotected to give the corresponding free acid or salt. In some cases, however, it has been found particularly convenient first to deprotect the isomeric mixture to give an isomeric mixture of the free acid or salt of formula (I), followed by fractional recrystallisation to give the desired acid or salt isomer. Where *D isomer of formula (I) is desired, it is preferred to use the corresponding *D isomer of the intermediate of formula (IIIA), (IIIB) or (IIIC).

A carboxyl group may be regenerated from any of the above esters by usual methods appropriate to the particular $R^X$ group, for example, acid- and base-catalysed hydrolysis, or by enzymically-catalysed hydrolysis, or by hydrogenolysis under conditions wherein the remainder of the molecule is substantially unaffected. For example, in the case of acetonyl, by hydrolysis in acetonitrile with 0.1M aqueous potassium hydroxide solution.

Pharmaceutically acceptable salts may be prepared from such acids by treatment with a base, after a conventional work-up if necessary. Suitable bases include sodium hydrogen carbonate to form sodium salts.

Crystalline forms of the compounds of formula (I) where R is a salt forming cation may for example be prepared by dissolving the compound (I) in the minimum quantity of water, suitably at ambient temperature, then adding a water miscible organic solvent such as a ($C_{1-6}$) alcohol or ketone such as ethanol or acetone, upon which crystallisation occurs and which may be encouraged for example by cooling or trituration.

Compounds of formulae (II), (IIIA), (IIIB) and (IIIC) are known compounds or may be prepared by procedures analogous to those described in the prior art references listed above.

Novel compounds of formula (IIIA), (IIIB) and (IIIC), which are α-amino acids, may be prepared by any conventional amino acid synthesis, for example compounds of formula (IIIA) and (IIIC) may be prepared from the corresponding α-keto ester $R_1^{A'}$— or $R_1^{C'}$—CO—$CO_2R^X$ via the oxime ester $R_1^{A'}$— or $R_1$,—C(=N—OH)—$CO_2R^X$ by conventional routes. The α-keto ester is obtainable from the $R_1^{A'}$— or $R_1^{C'}$—H, $R_1^{A'}$— or $R_1^{C'}$— $CH_2CO_2R^X$, or $R_1^{A'}$— or $R_1^{C'}$—$CO_2R^X$ by routine methods (J. March, vide infra). Alternatively the compounds of formula (IIIA) or (IIIC) may be prepared from the aldehyde intermediate $R_1^{A'}$— or $R_1^{C'}$—CHO by the Strecker synthesis [cf. Advanced Organic Chemistry; Mechanism and Structure, 4th Edn, by J. March, Section 6–50, p.965; 1992, John Wiley and Sons Inc, ISBN 0-471-60180-2] or by the method of Monianari et al. (Synthesis 1979, 26). The invention also extends to novel compounds of formula (IIIA), (IIIB) and (IIIC).

A compound of formula (I), particularly (IB), (IC or (ID), or a salt, solvate or in vivo hydrolysable ester thereof, may be administered in the form of a pharmaceutical composition together with a pharmaceutically acceptable carrier and the invention also relates to such compositions. The compounds of formula (I) have metallo-β-lactamase inhibitory properties, and are useful for the treatment of infections in animals, especially mammals, including humans, in particular in humans and domesticated (including farm)animals. The compounds may be used, for example, for the treatment of infections of, inter alia, the respiratory tract, the urinary tract, and soft tissues and blood, especially in humans.

The compounds may be used in combination with an antibiotic partner for the treatment of infections caused by metallo-β-lactamase producing strains, in addition to those infections which are subsumed within the antibacterial spectrum of the antibiotic partner. Metallo-β-lactamase producing strains include: *Pseudomonas aeruginosa, Klebsiella pneunoniae, Xanthomonas maltophilia, Bacteroides fragilis, Serratia marcescens, Bacteroides distasonis, Pseudomonas cepacia, Aeromonas hydrophila, Aeromonas sobria, Aeromonas salmonicida, Bacillus cereus, Legionella gormanii* and *Flavobacterium* spp.

It is generally advantageous to use a compound according to the invention in admixture or conjunction with a carbapenem, penicillin, cephalosporin or other β-lactam antibiotic and that can result in a synergistic effect, because of the metallo-β-lactamase inhibitory properties of the compounds according to the invention. In such cases, the compound of formula (I) and the β-lactam antibiotic can be administered separately or in the form of a single composition containing both active ingredients as discussed in more detail below. The compositions of the invention include those in a form adapted for oral, topical or parenteral use and may be used for the treatment of bacterial infection in mammals including humans. The compounds of formula (I) are particularly suitable for parenteral administration.

The compounds of formula (I) may be formulated for administration in any convenient way for use in human or veterinary medicine, by analogy with other antibiotics and other β-lactam antibiotic/β-lactamase inhibitor combinations.

The composition may be formulated for administration by any route, such as oral, topical or parenteral. The compositions may be in the form of tablets, capsules, powders, granules, lozenges, creams or liquid preparations, such as oral or sterile parenteral solutions or suspensions.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

Tablets and capsules for oral administration may be in unit dose presentation form, and may contain conventional excipients such as binding agents, for example syrup, acacia, gelatin, sorbitol, tragacanth, or polyvinylpyrollidone; fillers, for example lactose, sugar, maize-starch, calcium phosphate, sorbitol or glycine; tabletting lubricants, for example magnesium stearate, talc, polyethylene glycol or silica, disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing.

Advantageously, agents such as a local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilisation cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% by weight, preferably from 10–60% by weight, of the active material, depending on the method of administration. Where the compositions comprise dosage units, each unit will preferably contain from 50–500 mg of the active ingredient. The dosage as employed for adult human treatment will preferably range from 100 to 3000 mg per day, for instance 1500 mg per day depending on the route and frequency of administration. Such a dosage corresponds to 1.5 to 50 mg/kg per day. Suitably the dosage is from 5 to 20 mg/kg per day.

No toxicological effects are indicated when a compound of formula (I) or a pharmaceutically acceptable salt thereof is administered in the above-mentioned dosage range.

A composition according to the invention may comprise a compound of formula (I), more particularly (IB), (IC) or (ID), or a salt, solvate or in vivo hydrolysable ester thereof together with one or more additional active ingredients or therapeutic agents, for example a β-lactam antibiotic such as a carbapenem, penicillin or cephalosporin or pro-drug thereof. Carbapenems, penicillins, cephalosporins and other β-lactam antibiotics suitable for co-administration with the compound of formula (I)— whether by separate administration or by inclusion in the compositions according to the invention—include both those known to show instability to or to be otherwise susceptible to metallo-β-lactamases and also those known to have a degree of resistance to metallo-β-lactamases.

A serine β-lactamase inhibitor such as clavulanic acid, sulbactam or tazobactam may also be co-administered with the compound of the invention and the β-lactam antibiotic, either by separate administration, or co-formulation with one, other or both of the compounds of the invention and the β-lactarn antibiotic.

Examples of carbapenems that may be co-administered with the compounds according to the invention include imipenem, meropenem, biapenem, BMS181139 ([4R-[4alpha,5beta,6beta(R*)]]-4-[2-[(aminoiminomethyl) amino]ethyl]-3-[(2-cyanoethyl)thio)-6-(1-hydroxyethyl)-7-oxo-1-azabicyclo[3.2.0]hept-2-ene-2-carboxylic acid), BO2727 ([4R-3[3S*,5S*(R*)],4alpha,5beta,6beta(R*)]]-6-

(1-hydroxyethyl)-3-[[5-[1-hydroxy-3-(methylamino) propyl]-3-pyrrolidinyl]thio]-4-methyl-7-oxo-1-azabicyclo [3.2.0] hept-2-ene-2-carboxylic acid monohydrochloride), ER35786 ((1R, 5S, 6S)-6-[1(R)-Hydroxymethyl]-2-[2(S)-[1 (R)-hydroxy-1-[pyrrolidin-3(R)-yl] methyl]pyrrolidin4(S)-ylsulfanyl]-1-methyl-1-carba-2-penem-3-carboxylic acid hydrochloride) and S4661 ((1R,5S,6S)-2-[(3S,5S)-5-(sulfamoylaminomethyl) pyrrolidin-3-yl]thio-6-[(1 R)-1-hydroxyethyl]-1-methylcarbapen-2-em-3-carboxylic acid).

Examples of penicillins suitable for co-administration with the compounds according to the invention include benzylpenicillin, phenoxymethylpenicillin, carbenicillin, azidocillin, propicillin, ampicillin, amoxycillin, epicillin, ticarcillin, cyclacillin, pirbenicillin, azlocillin, mezlocillin, sulbenicillin, piperacillin, and other known penicillins. The penicillins may be used in the form of pro-drugs thereof, for example as in vivo hydrolysable esters,for example the acetoxymethyl, pivaloyloxymethyl, α-ethoxycarbonyloxyethyl and phthalidyl esters of ampicillin, benzylpenicillin and amoxycillin; as aldehyde or ketone adducts of penicillins containing a 6-α-aminoacetamido side chain (for example hetacillin, metampicillin and analogous derivatives of amoxycillin); and as α-esters of carbenicillin and ticarcillin, for example the phenyl and indanyl α-esters.

Examples of cephalosporins that may be co-administered with the compounds according to the invention include, cefatrizine, cephaloridine, cephalothin, cefazolin. cephalexin, cephacetrile, cephapirin, cephamandole nafate, cephradine, 4-hydroxycephalexin, cephaloglycin, cefoperazone, cefsulodin, ceftazidime, cefuroxime, cefmetazole, cefotaxime, ceftriaxone, and other known cephalosporins, all of which may be used in the form of pro-drugs thereof.

Examples of β-lactam antibiotics other than penicillins and cephalosporins that may be co-administered with the compounds according to the invention include aztreonam, latamoxef (Moxalactam—Trade Mark), and other known β-lactam antibiotics, all of which may be used in the form of pro-drugs thereof.

Particularly suitable penicillins for co-administration with the compounds according to the invention include ampicillin, amoxycillin, carbenicillin, piperacillin, azlocillin, mezlocillin, and ticarcillin. Such penicillins may be used in the form of their pharmaceutically acceptable salts, for example their sodium salts. Alternatively, ampicillin or amoxycillin may be used in the form of fine particles of the zwitterionic form (generally as ampicillin trihydrate or amoxycillin trihydrate) for use in an injectable or infusable suspension. for example, in the manner hereinbefore described in relation to the compounds according to the invention. Amoxycillin, for example in the form of its sodium salt or the trihydrate, is particularly preferred for use in synergistic compositions according to the invention.

Particularly suitable cephalosporins for co-administration with the compounds according to the invention include cefotaxime and ceftazidime, which may be used in the form of their pharmaceutically acceptable salts, for example their sodium salts.

A compound of formula (I) may be administered to the patient in conjunction with a β-lactam antibiotic such as a carbapenem, penicillin or cephalosporin in a synergistically effective amount.

The compounds of formula (I) may suitably be administered to the patient at a daily dosage of from 0.7 to 50 mg/kg of body weight. For an adult human (of approximately 70 kg body weight), from 50 to 3000 mg, preferably from 100 to 1000 mg, of a compound according to the invention may be administered daily, suitably in from 1 to 6, preferably from 2 to 4, separate doses. Higher or lower dosages may, however, be used in accordance with clinical practice.

When the compositions according to the invention are presented in unit dosage form, each unit dose may suitably comprise from 25 to 1000 mg, preferably from 50 to 500 mg, of a compound according to the invention. Each unit dose may, for example, be 62.5, 100, 125, 150, 200 or 250 mg of a compound according to the invention.

When the compounds of formula (I) are co-administered with a penicillin, cephalosporin, carbapenem or other β-lactam antibiotic, the ratio of the amount of the compound according to the invention to the amount of the other β-lactam antibiotic may vary within a wide range. The said ratio may, for example, be from 100:1 to 1:100; more particularly, it may, for example, be from 2:1 to 1:30.

The amount of carbapenem, penicillin, cephalosporin or other β-lactam antibiotic in a synergistic composition according to the invention will normally be approximately similar to the amount in which it is conventionally used per se, for example from about 50 mg, advantageously from about 62.5 mg, to about 3000 mg per unit dose, more usually about 125, 250, 500 or 1000 mg per unit dose.

The present invention further provides a compound of formula (I), more particularly (IB), (IC) or (ID), or a pharmaceutically acceptable salt, solvate or in vivo hydrolysable ester thereof for use in the treatment of bacterial infections.

The present invention also includes the use of a compound of formula (I), more particularly (IB), (IC) or (ID), or a pharmaceutically acceptable salt, solvate or in vivo hydrolysable ester thereof, in the manufacture of a medicament for the treatment of bacterial infections.

The present invention also includes the use of a compound of formula (I), more particularly (IB), (IC) or (ID), or a pharmaceutically acceptable salt, solvate or in vivo hydrolysable ester thereof as a metallo-β-lactamase inhibitor.

All the above compositions and methods may optionally include a serine β-lactamase inhibitor as above described.

The compounds of the present invention are active against metallo-β-lactamase enzymes produced by a wide range of organisms including both Gram-negative organisms and Gram-positive organisms.

The following Examples illustrate compounds useful in the present invention, and intermediates in their preparation. (All temperatures are in ° C.).

EXAMPLES

Description 1

(S)-Acetylthiosalicylic Acid

To a stirred solution of thiosalicylic acid (1.54 g. 10 mmol) in dichloromethane (30 ml) at room temperature was added triethylamine (3.1 ml, 22 mmol), acetic anhydride (0.94 ml, 10 mmol) and 4-dimethylaminopyridine (5 mg). After 2 h the solution was washed with 1M hydrochloric acid and water. The organic layer was dried ($MgSO_4$) and evaporated to give the desired product (1.71 g, 92%). $v_{max}$ ($CH_2Cl_2$) 1697cm$^{-1}$. δ ($CD_3COCD_3$) 2.39 (3H, s), 7.62 (3H, m), 7.99 (1H, m).

Description 2

(S)-N-(S-Acetylthiosalicyl)-5,5-dimethylthiazolidin-4-carboxylic acid

To a stirred suspension of the acid from Description 1 (196 mg, 1 mmol) in dichloromethane (2 ml) at room temperature was added oxalyl chloride (0.1 ml) and N,N-dimethylformamide (1 drop). After 30 minutes the solution was evaporated. The acid chloride was re-evaporated from toluene (2×2 ml). The acid chloride in dichloromethane (2 ml) was added dropwise to a stirred solution of (S)-5,5-dimethylthiazolidin-4-carboxylic acid (161 mg, 1 mmol) (*J. Am. Chem. Soc.*, 1949, 71, 1137).and triethylamnine (0.28 ml, 2.2 mmol) in dichloromethane (2 ml) at room temperature. After 1 h the solution was washed with 1M hydrochloric acid and water. The organic layer was dried (MgSO$_4$) and evaporated. The residue was flash chromatographed on silica and eluted with 0% grading to 20% ethanol in ethyl acetate to give the desired product (100 mg, 29%). $v_{max}$ (CH$_2$Cl$_2$) 1705, 1647 and 1270cm$^{-1}$. δ(CD$_3$OD) 1.53 (3H, s), 1.66 (3H, s), 2.43 (3H, s), 4.37 and 4.41 (2×xs, 1H), 4.56 (2H, m), 7.58 (4H, m), EIMS M$^+$339.

Description 3
2-(R,S)-Acetylthiocydopentane-1-(R,S)-carboxylic acid

A solution of cyclopentene-1-carboxylic acid (500 mg) in thiolacetic acid (0.5 ml) was heated at 100° for 2h and then evaporated. The residue was flash chromatographed on silica and eluted with 3% grading to 5% methanol in dichloromethane to give the desired product (776 mg, 92%). 6 (CDCl$_3$) 1.55–2.35 (6H, m), 2.32 (3H, s), 2.77 and 3.17 (1H, 2×m), 3.97 (1H, m).

Description 4
N-[2-(R,S)-Acetylthio-1-(R,S)-cyclopentancarbonyl]-5,5-dimethylthiazolidin-4-(S)-carboxylic acid.

A stirred solution of the acid from Description 3 (392 mg) in dichloromethane (5 ml) was converted to its acid chloride using oxalyl chloride (0.35 ml) and N,N-dimrthylformamide (1 drop) by the method used in Description 2. The acid chloride was coupled to (S)-5,5-dimethylthiazolidin-4-carboxylic acid (610 mg) in the presence of triethylamine (1.07 ml) in dichloromethane (10 ml) using the conditions and work-up as for Description 2. The desired product was isolated by flash chromatography on silica eluting with 3% grading to 5% methanol in dichloromethane (390 mg, 57%). δ (CDCl$_3$) 1.40–2.40 (15H, m), 2.97 and 3.35 (1H, 2×m), 4.05 (1H, m), 4.45–4.95 (3(1H, br). EIMS M$^+$331.

Description 5
Methyl N-(1-cyclohexene-1-carbonyl)-D-phenylglycinate a) D-Phenylglycine methyl ester hydrochloride Acetyl chloride (4 ml) was added cautiously and dropwise to methanol (20 ml) at 0° C. over 2 minutes. When the addition was completed, D-phenylglycine (1 g, 5.9 mmol, Aldrich) was introduced in a single portion. The mixture was stirred until dissolved then allowed to stand at RT for 24 hours. The solvent was evaporated then coevaporated twice from toluene to afford the title compound as a white crystalline solid in quantitative yield. The title compound was obtained as a white crystalline solid in quantitative yield with an identical n.m.r. spectrum to the L-isomer.

b) Title compound

To a stirred solution of cyclohexane-1-carboxylic acid (1.09 g) (Lancaster) in dichloromethane (10 ml) was added oxalyl chloride (2 ml) and N,N-dimethylformamide (1 drop). After 30 minutes the solution was evaporated and then re-evaporated from dichloromethane (2×10 ml). The acid chloride in dichloromethane was added dropwise to an ice cold mixture of D-Phenylglycine methyl ester hydrochloride (1.74 g) from a) and triethylamine (2.9 ml) in dichloromethane (20 ml). Allowed to gain room temperature and stirred for 1 h. The reaction mixture was loaded directly on to a silica flash column and the title product eluted with 20% ethyl acetate in hexane (2.1 g, 89%). δ(CDCl$_3$) 1.52–1.74 (4H, m), 2.10–2.33 (4H, m), 3.74 (3H, s), 5.63 (1H, d, J=7.0 Hz), 6.65 (1H, d, J=7.0 Hz), 6.71 (1H, m), 7.25–7.45 (5H, m), ESIMS MH$^+$274.

Description 6
Methyl N-[2-(R,S)-acetylthio-1-(R,S)-cyclohexancarbonyl]-D-phenylglycinate A solution of the eneamide from Description 5 (1.2 g) in thiolacetic acid (3 ml) was stood at room temperature for 5 days and evaporated. The residue was flash chromatographed on silica and the title product eluted with 5% grading to 30% ethyl acetate in hexane (1.4 g, 91%). δ(CDCl$_3$) 1.25–2.05 (8H, m), 2.15 and 2.28 (3H, 2×s), 2.68 (1H, m), 3.70 and 3.72 (3H, 2×s), 4.11 (1H, m), 5.52 and 5.55 (1H, 2×d, j=7.0 Hz), 6.57 and 6.60 (1H, 2×d, 6.5 Hz), ESI MS MH$^+$350.

Description 7
Methyl N-(1-cydopentene-1-carbonyl)-D-phenylglycinate

Cyclopentene-1-carboxylic acid (0.56 g, 5 mmol) was converted to its acid chloride and then coupled to D-Phenylglycine methyl ester hydrochloride (1.01 g, 5 mmol) using the method of Description 5. The title product was eluted from a silica flash column using 15% grading to 25% ethyl acetate in hexane (1.0 g, 77%). δ(CDCl$_3$) 1.92–2.08 (2H, m), 2.45–2.68 (4H, m), 3.75 (3H, s), 5.65 (1H, d, J 7.0 Hz), 6.61 (2H, m), 7.26–7.44 (5H, m). EIMS MH$^+$260.

Description 8
Methyl N-[2-(R,S)acetylthio-1-(R,S)cyclopentancarbonyl]-D-phenylglycinate A solution of the ene amide from Description 7 (0.9 g) in thiolacetic acid (2 ml) was stood at room temperature for 24 h and then evaporated. The residue was flash chromatographed on silica and the title product eluted with 15% grading to 25% ethyl acetate in hexane (1.03 g, 88%). δ(CDCl$_3$) 1.50–2.40 (9H, m), 2.76 and 3.10 (1H, 2×m), 3.73 (3H, s), 3.70–4.08 (1H, m), 5.57 (1H, m), 6.33–6.58 and 7.30–7.77 (6H, 2×m). ESI MS MH$^+$336.

Description 9
2-Methoxycarbonylindanone

The desired compound was prepared from 1-indanone (5.58 g) using the method of H. O. House et al *J. Org. Chem.* 1970, 35, 647 (3.8 g, 47%). δ(CDCl$_3$), 3.13 (2H, m), 3.60 (1H, m), 3.64 (3H, s), 7.21–7.64 (4H, m), EIMS MH$^+$191.

Description 10
Methyl indene-2-carboxylate

A solution of the β-ketoester from Description 9 (3 g) in methanol (30 ml) was treated with sodium borohydride (0.6 g) portionwise over 10 minutes. After 1 h the solution was evaporated. The residue was redissolved in ethyl acetate, washed with 2M hydrochloric acid, water, saturated brine, dried (MgSO$_4$) and evaporated. The crude product was refluxed in benzene (100 ml) with 4-toluene sulphonic acid (100 mg) under Dean-Stark conditions for 7 h. The solution was evaporated and the residue flash chromatographed on silica. The desired product was eluted with 5% ethyl acetate in hexane (0.68 g, 25%). δ(CDCl$_3$) 3.69 (2H, s), 3.86 (3H, s), 7.31–7.56 (4H, m), 7.74 (1H, s). EIMS MH$^+$175.

Description 11
Indene-2-carboxylic acid

A solution of the ester from Description 10 (630 mg) in methanol (5 ml) was treated with sodium hydroxide (290 mg) in water (5 ml). After 2 days the methanol was evaporated and the aqueous washed with ether. The aqueous layer was acidified and extracted with ethyl acetate. The organic layer was washed with water, saturated brine, dried (MgSO$_4$) and evaporated to give the desired compound (500 mg, 86%). δ(CD$_3$SOCD$_3$) 3.63 (2H, s), 7.30–7.63 (4H, m), 7.69 (1H, s). EIMS [M−H] 159.

Description 12
Methyl N-(indene-2-carbonyl)-D-phenylglycinate
The acid from Description 11 (410 mg) was converted to its acid chloride and then coupled to D-Phenylglycine methyl ester hydrochloride (520 mg) using the method of Description 5. The title product was eluted from a silica column using 20% grading to 30% ethyl acetate in hexane (500 mg, 64%). δ(CDCl$_3$) 3.69 (2H, s), 3.75 (3H, s), 5.71 (1H, d J=7 Hz), 6.87 (1H, d, J=6.8 Hz), 7.22–7.54 (5H, m). EIMS MH$^+$308.

Description 13
Methyl N-[1-(R,S)-acetylthio-2-(R,S)-indanecarbonyl]-D-phenylglycinate
A solution of the ene amide from Description 12 (435 mg) in thiolacetic acid (2 ml) was stood at room temperature for 6 days and then evaporated. The residue was flash chromatographed on silica and the title product eluted with 15% grading to 30% ethyl acetate in hexane (290 mg, 53%). δ(CDCl$_3$) 2.40–2.46 (3H, m), 3.06–3.78 (6H, m), 5.10–5.78 (2H, m), 6.67, 6.97, 7.95 and 8.22 (1H, 4×m), 7.15–7.60 (9H, m). ESI MS MH$^+$384, MNa$^+$406.

Description 14
2-Methoxycarbonyl-1-tetralone
The desired compound was prepared from 1-tetralone (6.64 ml) using the method of Description 9 (2.92 g, 30%). δ(CDCl$_3$) 2.66 (2H, t, J=7.0 Hz), 2.91 (2H, t, J=7.0 Hz), 3.92 (3H, s), 7.20–7.95 (4H, m), 12.49 (1H, s). EIMS [M−H] 203 MH$^+$205.

Description 15
2-Methoxycarbonyltetralin-1-ene
The β-keto ester from Description 14 (1.4 g) was converted to the desired compound by the method of Description 10 (0.5 g, 39%). δ(CDCl$_3$) 2.54 (2H, t, J=6.3 Hz), 2.80 (2H, t, J=6.5 Hz), 3.75 (3H, s), 7.07–7.21 (4H, m), 7.46 (1H,s), EIMS MH$^+$189.

Description 16
Tetralin-1-ene-2-carboxylic acid
The ester from Description 15 (450 mg) was hydrolysed to the desired compound by the method of Description 11 except that the reaction was refluxed for 8h (370 mg, 89%). δ(CD$_3$SOCD$_3$) 2.46 (2H. t, J=7.9 Hz), 2.81 (2H, t, J=7.9 Hz), 7.27 (4H, m), 7.47 (1H, s). EIMS [M−H] 173.

Description 17
Methyl N-(tetralin-1-ene-2-carbonyl)-D-phenylglycinate
The acid from Description 16 (300 mg) was converted to its acid chloride and then coupled to methyl (D)-phenylglycinate hydrochloride (350 mg) using the method of Description 5 (508 mg, 92%). δ(CDCl$_3$) 2.46 (2H, t, J=8.0 Hz), 2.75 (2H, t, J=8.0 Hz), 3.63 (3H, s), 5.57 (1H, d, J =6.8 Hz), 6.75 (1H, d, J=6.8 Hz), 6.76–7.32 (5H, m). EIMS MH$^+$322.

Description 18
Methyl N-[ -(R,S)-acetylthio-2-(R,S)-tetralincarbonyl]-D-phenylglycinate
A solution of the ene amide from Description 17 (300 mg) in thiolacetic acid (2 ml) was refluxed for 4 days and then evaporated. The residue was flash chromatographed on silica and the title product eluted with 20% grading to 30% ethyl acetate in hexane (140 mg, 38%). δ(CDCl$_3$) 1.65–3.10 (8H, m), 3.63 (3H, m), 4.95–5.60 (2H, m), 6.56–7.38 (10H, m). ESIMS MH$^+$398 MNa+420.

Description 19
Methyl N-(1-cydohexenecarbonyl)-4-hydroxy-D-phenylglycinate
A solution of cyclohexene-1-carboxylic acid (364 mg) in dichloromethane (5 ml) was treated with oxalyl chloride (0.28 ml) and N,N-dimethylformamide (0.1 drop). Stirred for 30 minutes at room temperature and then evaporated. Re-evaporated from dichloromethane (2×5 ml). The acid chloride in dichloromethane (5 ml) was added dropwise to a solution of methyl (R)-4-hydroxyphenylglycinate (488 mg) and triethylamine (0.44 ml) at room temperature. Methyl (D)-4hydroxyphenylglycinate was prepared by the action of triethylamine on the glycinate hydrochloride, which was, in turn, obtained obtaned from the commercially available (D)-4-hydroxyphenylglycine using acetyl chloride in methanol. After 30 minutes the mixture was loaded directly onto a silica flash column. The title product was eluted with 20% to 100% ethyl acetate in hexane (605 mg, 72%). δ(CD$_3$SOCD$_3$) 1.55 (4H, m), 2.13 (4H, m), 3.60 (3H, s), 5.32 (1H, d, J=6.25 Hz), 6.60 (1H, bs), 6.73 and 7.15 (4H, ABq, J=8.5 Hz), 8.21 (1H, d, J=6.25 Hz), 9.52 (1H, s). EIMS [M−H] 288.

Description 20
Methyl N-(1-cyclohexenecarbonyl)-4-(4-methoxycarbonylbenzyloxy)-D-phenyl-glycinate
A mixture of the compound from Description 19 (289 mg), triphenylphosphine (328 mg) and methyl 4-hydroxymethylbenzoate (166 mg) in tetrahydrothieo (10 ml) at room temperature was treated with diethyl azodicarboxylate (0.2 ml). After 30 minutes the mixture was evaporated and the residue flash chromatographed on silica. The title product was eluted with 25% grading to 30% ethyl acetate in hexane (184 mg, 42%). δ(CDCl$_3$) 1.55–2.35 (8H m), 3.75 (3H, s), 3.94 (3H, s), 5.13 (2H, s), 5.58 J=6.8 Hz), 6.62 (1H, d, J=6.8 Hz), 6.71 (1H, m), 6.95 and 7.32 (4H, ABq, 11.5 Hz), 7.49 and 8.07 (4H, ABq, 8.3 Hz).

Description 21
Methyl N-[Z-(R,S)-acetyltiiio-1-(R,S) cyclohexanecarbonyl)-4-(4-methoxy-carbonylbenzyioxy)-D-phenylglycinate
A solution of the eneamide from Description 20 in thiolacetic acid was stood at room temperature for 7 days and then evaporated. The residue was flash chromatographed on silica and the title product was eluted with 20% grading to 35% ethyl acetate in hexane (150 mg, 75%). δ(CDCl$_3$) 1.20–1.90 (8H, m), 2.04–2.20 (3H, 2×s), 2.57 (1H, m), 3.59 and 3.61 (3H, 2××s), 3.82 (3H, s), 4.00 (1H, m), 5.00 (2H, s), 5.36 (1H, m), 6.41 (1H, m), 6.81, 7.16, 7.37 and 7.94 (8H, 4×m). ESIMS MH$^+$514 MNa$^+$536.

Example 1
Ammonium (S)-N-(thiosalicyl)-5,5-dimethylthiazolidin-4-carboxylate
A solution of (S)-N-(S-acetylthiosalicyl)-5,5-dimethylthiazolidin-4-carboxylic acid (from Description 2)(250 mg) in ·880 ammonia solution (2 ml) was stood at room temperature for 30 minutes and then evaporated. The residue was flash chromatographed on silica and eluted with 5% grading to 25% methanol in dichloromethane to give the title product E1 containing ammonium acetate (230 mg). $v_{max}$ (CH$_2$Cl$_2$) 1704, 1676 and 1615cm$^{-1}$. $\delta$(CD$_3$SOCD$_3$) inter alia 1.36 (3H, s), 1.58 (3H, s), 1.74 (3H, s), 4.36 (1H, s), 4.42 and 4.86 (2H, ABq, J 9.2 Hz), 6.65–7.29 (4H, m).

Example 2

5,5-Dimethyl-N-12-(R,S)-mercapto-1-(R,S)-cyclopentancarbonyl]-thiiazolidin-4-(S)-carboxylic acid A solution of the acetylthio compound from Description 4 in ·880 ammonia solution was stood at room temperature for 30 minutes and then evaporated. The residue was redissolved in ethyl acetate, washed with 1M hydrochloric acid, dried (MgSO$_4$) and evaporated. The residue was flash chromatographed on silica and the title compound E2 eluted with 3% grading to 5% methanol in dichloromethane (207mg, 99%). $v_{max}$ (CH$_2$Cl$_2$) 2970, 1721 and 1648cm$^{-1}$. $\delta$(CD$_3$SOCD$_3$) 1.40–3.73 (14H, m), 4.27–5.08 (3H, m). EIMS M$^+$289.

Example 3

N-[2-(R,S)-Mercapto-1-(R,S)-cyclohexancarbonyl]-D-phenylglycine

The ester from Description 6 (1.25 g) in methanol (20 ml) at room temperature was treated with a solution of sodium sulphide nonahydrate (2.58 g) in water (20 ml). After 15 minutes the mixture was diluted with ethyl acetate, washed with 1M hydrochloric acid, water (3×), saturated brine, dried (MgSO$_4$) and evaporated. The residue was flash chromatographed on silica and the title product E4 eluted with 5% grading to 10% methanol in dichloromethane (710 mg, 68%). $\delta$(CD$_3$SOCD$_3$), 1.13–2.32 (9H, m), 2.71 (1H, m), 3.45–3.72 (1H, m), 5.32 (1H, m), 7.38 (5H, m), 8.43 (1H, m), 12.84 (1H, bs). ESIMS MH$^+$294.

Example 4

N-[2-(R,S)-Mercapto-1-(R,S)-cyclopentanoyl]-D-phenylglycine

The ester from Description $\delta$(0.84 g) was deprotected with sodium sulphide nonahydrate (1.80g) as described in Example 3 to give the title E4 (0.58 g, 83%). $\delta$(CD$_3$SOCD$_3$) 1.40–3.63 (9H, m), 5.29 (1H, d, J=6.8 Hz), 7.22–7.48 (5H, m) (11H, m). EIMS M$^+$279.

Example 5

N-[1-(R,S)-Mercapto-2-(R,S)-indanecarbonyl]-D-phenylglycine

The ester from Description 13 (280 mg) was deprotected with sodium sulphide nonahydrate (520 mg) as described in Example 3 to give the title compound E5 (143 mg, 60%). $\delta$(CD$_3$SOCD$_3$) 2.60–3.75 (4H, m), 4.45–4.85 (1H, m), 5.90 (1H, m (9H, m), 8.62–8.95 (1H, m). ESIMS [M-H] 326.

Example 6

N-[1-(R,S)-Mercapto-2-(R,S)-tetralincarbonyl]-D-phenylglycine

The ester from Description 18 (130 mg) was deprotected with sodium sulphide nonahydrate (236 mg) as described in Example 3 to give the title compound E6 (110 mg, 99%). $\delta$(CDCl$_3$) 1.85–3.08 (6H, m), 4.40–4.79 (1H, m), 5.65 (1H, m), 6.70–7.70 (10H, m). ESIMS [M-H] 340.

Example 7

N-[2-(R,S)-Mercapto-1-(R,S)-cyclohexanecarbonyl]-4-(4-carboxybenzyloxy)-D-phenylglcine A solution of the ester from Description 21 (150 mg) in methanol (5 ml) was treated with a solution of sodium sulphide nonahydrate (421 mg) in water (5 ml). After 2.5 h at room temperature the mixture was diluted with ethyl acetate (20 ml), washed with 2M hydrochloric acid, water, brine, dried (MgSO$_4$) and evaporated to give the title product E7 (110 mg, 85%). $\delta$(CD$_3$COCD$_3$) 1.10–1.95 (8H, m), 2.64 (1H, m), 3.51 (1H, m), 5.11 (2H, bs), 5.31 (1H, m), 6.90, 7.26, 7.47 and 7.92 (9H, 4×m). ESIMS [M-H] 442.

BIOLOGICAL ACTIVITY

I$_{50}$ screen

The inhibitory activity of the compounds of the invention was measured in 25 μM PIPES pH 7 buffer at 10 concentrations (1000, 333, 111, 37, 12.3, 4.1, 1.4, 0.46, 0.15 and 0.05 μM) at 37° C. using nitrocefin (91 μM final concentration) as the reporter substrate. The assays were performed with a 5 minute preincubation of enzyme and inhibitor and were conducted in the presence of added zinc sulphate (Zn$^{2+}$100 μM, final concentration). The methodology is described in detail in the following references: Payne et al (1991), *J. Antimicrob. Chemother.*, 28:255; Payne et al (1994), *Antimicrob. Agents and Chemother.*, 38:767.

Results

The compounds of the examples exhibit 150 values against *B.fragilis* CfiA metallo-β-lactamase of <1000 mM. The I$_{50}$ value for example E3 is <1 μM.

What is claimed is:

1. A compound of formula (ID) or a pharmaceutically acceptable salt, solvate or in vivo hydrolysable ester thereof:

ID wherein

R is hydrogen, a salt forming cation or an in vivo hydrolysable ester-forming group;

R$_1^A$ is unsubstituted or substituted aryl or heteroaryl;

R$_2^A$ is hydrogen, (C$_{1-6}$)alkyl or aryl(C$_{1-6}$)alkyl;

R$_3$ and R$_5$ together complete a carbocyclic ring having 4 to 8 ring atoms, which may be saturated, unsaturated or aromatic, optionally fused to a phenyl ring, and optionally substituted by 1–3 halo, phenyl, (C$_{1-6}$)alkoxy optionally substituted by 1–3 halo, hydroxy(C$_{1-6}$)alkyl, mercapto(C$_{1-6}$)alkyl, hydroxy, CO$_2$R$_7$, N(R$_7$)$_2$ or CON(R$_7$)$_2$ where each R$_7$ is independently hydrogen or (C$_{1-6}$)alkyl, OCONH$_2$, nitro, (C$_{1-6}$) alkylcarbonyloxy, (C$_{1-6}$)alkoxycarbonyl(C$_{1-6}$)alkyl, formyl, or (C$_{1-6}$) alkylcarbonyl groups; and R$_4$ is hydrogen, or an in vivo hydrolysable acyl group.

2. A compound according to claim 1 wherein R$_1^A$ is from phenyl optionally substituted with up to five, preferably up to three, groups selected from the group consisting of halogen, mercapto, (C$_{1-6}$)alkyl optionally substituted by 1–3 halo, phenyl, (C$_{1-6}$) alkoxy optionally substituted by 1–3 halo, hydroxy(C$_{1-6}$)alkyl, mercapto(C$_{1-6}$)alkyl, hydroxy, amino, nitro, carboxy, (C$_{1-6}$) alkylcarbonyloxy, (C$_{1-6}$) alkoxycarbonyl, formyl and (C$_{1-6}$) alkylcarbonyl groups, indolyl, thienyl, isoimidazolyl, thiazolyl, furyl and benzothienyl.

3. A compound according to claim 1 wherein R$_1^A$ is unsubstituted phenyl.

4. A compound according to claim 1 wherein R$_2^A$ is hydrogen, methyl or benzyl.

5. A compound according to claim 1 wherein R$_3$ and R$_5$ together represent (CH$_2$)$_3$ or (CH$_2$)$_4$ optionally fused to phenyl, or together complete a phenyl ring.

6. A compound according to claim 1 wherein $R_4$ is hydrogen, lower alkylcarbonyl, optionally substituted benzoyl or optionally substituted phenyl lower alkyl carbonyl.

7. A compound according to claim 1 wherein R is hydrogen.

8. A compound according to claim 1 wherein the stereochemistry at the carbon atom marked * is D-.

9. A compound which is:

N-[2-(R,S)- mercapto-1-(R,S)-cyclopentanoyl]-D-phenylglycine;

N-[1-(R,S)- mercapto-2-(R,S)-indanecarbonyl]-D-phenylglycine;

N-[1-(R,S)- mercapto-2-(R,S)-tetralincarbonyl]-D-phenylglycine;

or a pharmaceutically acceptable salt, solvate or *in vivo* hydrolysable ester of any of the foregoing compounds.

10. A pharmaceutical composition comprising a compound of claim 1 or a pharmaceutically acceptable salt, solvate or in vivo hydrolysable ester thereof together with a β-lactam antibiotic and a pharmaceutically acceptable carrier.

11. A pharmaceutical composition comprising a compound according to claim 1 together with a pharmaceutically acceptable carrier.

12. A composition according to claim 10 wherein the β-lactam antibiotic is a carbapenem selected from imipenem, meropenem, biapenem, BMS181139 ([4R-[4alpha,5beta,6beta(R*)]]-4-[2-[(aminoiminomethyl)amino]ethyl]-3-[(2-cyanoethyl)thio]-6-(1-hydroxyethyl)-7-oxo-1-azabicyclo[3.2.0]hept-2-ene-2-carboxylic acid), BO2727 ([4R-3[3S*, 5S*(R*)], 4alpha, 5beta,6beta(R*)]]-6-(1-hydroxyethyl)-3-[[5[1-hydroxy-3-(methylamino) propyl]-3-pyrrolidinyl]thio]-4-methyl-7-oxo-1-azabicyclo [3.2.0] hept-2-ene-2-carboxylic acid monohydrochloride), ER35786 ((1R, 5S, 6S)-6-[1(R)-Hydroxymethyl]-2-[2(S)-[1 (R)-hydroxy-1-[pyrrolidin-3(R)-yl] methyl]pyrrolidin-4(S)-ylsulfanyl]-1-methyl-1-carb-2-penem-3-carboxylic acid hydrochloride) and S4661 ((1R,5S,6S)-2-[(3S,5S)-5-(sulfamoylaminomethyl) pyrrolidin-3-yl]thio-6-[(1R)-1-hydroxyethyl]-1-methylcarbapen-2-em-3-carboxylic acid).

13. A method of treating bacterial infections in humans or animals which comprises administering, in combination with a β-lactam antibiotic, a therapeutically effective amount of a compound of Formula ID or a pharmaceutically acceptable salt, solvate or in vivo hydrolysable ester thereof to a subject in need thereof:

ID

wherein

R is hydrogen, a salt forming cation or an in vivo hydrolysable ester-forming group;

$R_1^A$ is unsubstituted or substituted aryl or heteroaryl;

$R_2^A$ is hydrogen, $(C_{1-6})$alkyl or aryl$(C_{1-6})$alkyl;

$R_3$ and $R_5$ together complete a carbocyclic ring having 4 to 8 ring atoms, which may be saturated, unsaturated or aromatic, optionally fused to a phenyl ring, and optionally substituted by 1–3 halo, phenyl, $(C_{1-6})$alkoxy optionally substituted by 1–3 halo, hydroxy$(C_{1-6})$alkyl, mercapto$(C_{1-6})$alkyl, hydroxy, $CO_2R_7$, $N(R_7)_2$ or $CON(R_7)_2$ where each $R_7$ is independently hydrogen or $(C_{1-6})$ alkyl, $OCONH_2$, nitro, $(C_{1-6})$ alkylcarbonyloxy, $(C_{1-6})$alkoxycarbonyl$(C_{1-6})$ alkyl, formyl, or $(C_{1-6})$ alkylcarbonyl groups; and $R_4$ is hydrogen, or an in vivo hydrolysable acyl group.

14. The method according to claim 13 wherein $R_1^A$ is phenyl optionally substituted with up to five, preferably up to three, groups selected from the group consisting of halogen, mercapto, $(C_{1-6})$ alkyl optionally substituted by 1–3 halo, phenyl, $(C_{1-6})$ alkoxy optionally substituted by 1–3 halo, hydroxy$(C_{1-6})$alkyl, mercapto$(C_{1-6})$alkyl, hydroxy, amino, nitro, carboxy, $(C_{1-6})$ alkylcarbonyloxy, $(C_{1-6})$alkoxycarbonyl, formyl and $(C_{1-6})$ alkylcarbonyl groups, indolyl, thienyl, isoimidazolyl, thiazolyl, furyl and benzothienyl.

15. A compound according to claim 6 wherein $R_4$ is hydrogen.

* * * * *